United States Patent
Fukuya et al.

(10) Patent No.: US 7,246,013 B2
(45) Date of Patent: Jul. 17, 2007

(54) DATA PROCESSOR FOR USE IN CHROMATOGRAPHIC ANALYSIS

(75) Inventors: Shunji Fukuya, Ayase (JP); Genichi Uematsu, Sagamihara (JP)

(73) Assignee: Tosoh Corporation, Shunan-shi (JP)

( * ) Notice: Subject to any disclaimer, the term of this patent is extended or adjusted under 35 U.S.C. 154(b) by 0 days.

(21) Appl. No.: 11/337,006

(22) Filed: Jan. 23, 2006

(65) Prior Publication Data

US 2006/0167661 A1  Jul. 27, 2006

(30) Foreign Application Priority Data

Jan. 24, 2005 (JP) ............................ 2005-016009

(51) Int. Cl.
*G06F 19/00* (2006.01)
(52) U.S. Cl. ...................................... 702/32; 210/656
(58) Field of Classification Search .................... None
See application file for complete search history.

(56) References Cited

U.S. PATENT DOCUMENTS

| | | | |
|---|---|---|---|
| 6,581,020 B1 * | 6/2003 | Buote et al. ................. 702/123 |
| 6,613,224 B1 | 9/2003 | Strand | |
| 6,647,397 B2 * | 11/2003 | Parce ....................... 707/104.1 |
| 6,681,198 B2 * | 1/2004 | Buote et al. ................. 702/185 |
| 6,730,228 B2 * | 5/2004 | Petro et al. .................. 210/656 |
| 7,092,839 B2 * | 8/2006 | Buote et al. ................. 702/123 |
| 2003/0070988 A1 * | 4/2003 | Petro et al. .................. 210/656 |
| 2003/0080062 A1 * | 5/2003 | Petro et al. .................. 210/656 |
| 2003/0089663 A1 * | 5/2003 | Petro et al. .................. 210/656 |
| 2004/0016341 A1 * | 1/2004 | Tipler et al. .................... 95/82 |
| 2004/0035183 A1 * | 2/2004 | O'Brien et al. ............. 73/23.36 |
| 2004/0149010 A1 * | 8/2004 | Zilioli et al. ................ 73/23.41 |
| 2004/0168529 A1 * | 9/2004 | Carlson et al. ................ 73/866 |
| 2004/0260414 A1 * | 12/2004 | Barringer et al. ............. 700/90 |
| 2005/0010375 A1 * | 1/2005 | Gallagher ..................... 702/32 |
| 2005/0039602 A1 * | 2/2005 | Tipler et al. ................... 96/101 |
| 2005/0288872 A1 * | 12/2005 | Old et al. ....................... 702/30 |
| 2006/0099716 A1 * | 5/2006 | Tipler et al. ................. 436/161 |
| 2006/0144126 A1 * | 7/2006 | O'Brien et al. ............ 73/23.42 |
| 2006/0144171 A1 * | 7/2006 | Carlson et al. ................ 73/866 |
| 2006/0167661 A1 * | 7/2006 | Fukuya et al. .............. 702/185 |
| 2006/0213257 A1 * | 9/2006 | Togashi et al. ............. 73/61.55 |

FOREIGN PATENT DOCUMENTS

| | | |
|---|---|---|
| EP | 0 880 027 A2 | 11/1998 |
| JP | 2-127899 | 5/1990 |
| JP | 2004-309252 | 11/2004 |

OTHER PUBLICATIONS

"Code of Federal Regulations: Electronic Records, Electronic Signatures", Food and Drug Administration, XP-002384012, Apr. 1, 2002, p. 123.

* cited by examiner

*Primary Examiner*—Carol S. W. Tsai
*Assistant Examiner*—Mary Catherine Baran
(74) *Attorney, Agent, or Firm*—Oblon, Spivak, McClelland, Maier & Neustadt, P.C.

(57) ABSTRACT

A data processor for analyzing chromatograms in detail and collecting analysis-associated information necessary for verification of data validity throughout an analysis process. The data processor includes a first data collecting section which collects and records a detector output at every data sampling rate T1 for each sample injection, and a second data collecting section which collects and records the detector output and a monitor output indicating an analysis-associated condition at every data sampling rate T2 over a period from the start to the end of the chromatographic analysis; the data sampling rate T1 is shorter than the data sampling rate T2.

4 Claims, 2 Drawing Sheets

DATA PROCESSOR FOR USE IN CHROMATOGRAPHIC ANALYSIS

FIELD OF THE INVENTION

The present invention relates to a data processor for use in chromatographic analysis; and more particularly to a data processor advantageously used in chromatographic analysis in which a plurality of samples are successively injected for analysis.

PRIOR ART

Great strides have been made in the automation of chromatography apparatus by use of an autosampler for continuously injection many samples into the chromatography apparatus and a computer for collecting and processing various kinds of data. As chromatography has become widespread in such fields as the quality control of industrial and medical products and medical diagnosis, there has developed a strong need to enhance the reliability of analysis. For example, Federal rules (United States FDA's 21 CFR Part 11) require that all quality assurance systems for medical product development have audit trail capabilities to automatically record user operations such as the creation of electronic records and any corrections, deletions, etc. made to the electronic records. For chromatography apparatus also, there is a need to construct a system that eliminates the possibility of data falsification and ensures the validity of analysis results.

For example, Japanese Unexamined Patent Publication (Kokai) No. 2004-309252 discloses a data processor that collects not only all chromatograms during a continuous series of analyses but also analysis-associated information such as analysis conditions, a log of operations performed during the analysis process. Here, a parent file recording the entire analysis process is created, and from this parent file, each individual chromatogram related to each analysis can be extracted as a child file based on the time segment corresponding to that analysis.

DISCLOSURE OF THE INVENTION

When performing analyses by continuously injecting a plurality of samples into a chromatography apparatus, keeping the records of the entire analysis process by collecting and recording not only all detector outputs but also analysis-associated information, as disclosed in Japanese Unexamined Patent Publication (Kokai) No. 2004-309252, is extremely effective in eliminating the possibility of data falsification and ensuring the validity of analysis results. By so doing, it becomes possible to check for any changes that occurred between the injection of one sample and the injection of the next sample, such as a drop in pump pressure or any other changes externally made to the analysis conditions. However, when using the chromatography apparatus for purifying or separating substances or for continuously processing many samples for analysis, the analysis time becomes very long. Assuming the use of a computer for processing the data, if all the necessary data are to be recorded over the long analysis time, the data sampling rate at which to sample analysis data has to be made coarse, which poses a problem when it comes to detailed analysis of chromatograms.

An object of the present invention is to provide a data processor that not only makes it possible to analyze chromatograms in detail but can also collect analysis-associated information necessary for verification of data validity throughout the entire analysis process, even in cases where many samples are successively injected into the chromatography apparatus over a long period of time as described above.

BRIEF DESCRIPTION OF THE DRAWINGS

FIGS. 2(a) and 2(b) are diagrams showing the data processed by the data processor of the present invention and presented in the form of a chromatogram.

BEST MODE FOR CARRYING OUT THE INVENTION

Figure 1:
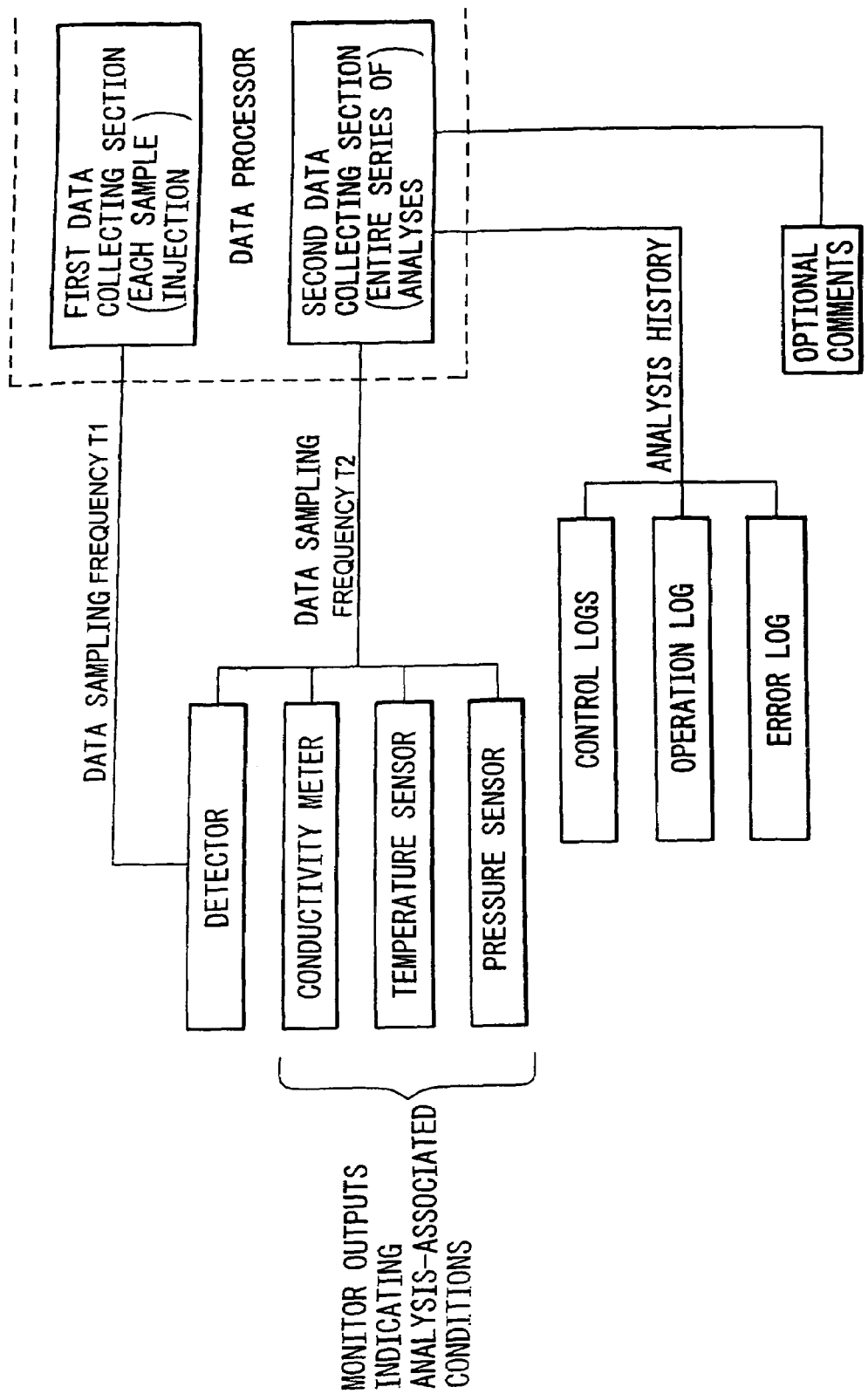
FIG. 1 is a diagram illustrating the flow of information around data collecting sections which constitute a feature of a data processor of the present invention.

The present inventor have conducted concentrated study by focusing on the point that data concerning the detector output that needs detailed analysis and data concerning the monitor output that indicates the analysis-associated condition are collected and recorded at respectively different data sampling rates, and have completed the data processor that solves the above problem. That is, the present invention provides a data processor for use in chromatographic analysis in which a sample is injected into a separation column and is detected by a detector, comprising: a first data collecting section which, for each sample injection, collects and records a detector output at every data sampling rate T1; and a second data collecting section which collects and records the detector output and a monitor output indicating an analysis-associated condition at every data sampling rate T2 over a period from the start to the end of the chromatographic analysis, wherein the data sampling rate T1 is shorter than the data sampling rate T2. The present invention is also characterized by the provision of such a data processor and a chromatogram display section which displays at least one output selected from the group consisting of the detector output that have been recorded by the data processor, the monitor output indicating the analysis-associated condition, analysis history, and optional comments.

The period over which the first data collecting section collects and records the detector output for each sample injection can be set as desired, but preferably the period is set so as to start when the sample is injected and to last until the time the last elution buffer is expected to be eluted; that is, the period should be set by considering such parameters as the sample volume injection, the flow rate, and the kind of the sample.

The detector output to be collected and recorded in the present invention can be any output that is usually used in chromatographic analysis, examples including the output of a spectrometer, the output of a fluorescence detector, etc. Further, the detector output need not be limited to any single index constituting a chromatogram; for example, two wavelength detection signals output from a Ultraviolet/visible spectrometer used in liquid chromatography may be used singly or in combination.

The period from the start to the end of the chromatographic analysis refers to the period from the start to the end of a series of analyses performed on arbitrarily specified one or more samples, and is not affected by the number of samples. Accordingly, the second data collecting section can collect and record the data over the entire series of analyses, thus making it possible to refer to the data between sample injections which can not be collected by the first data collecting section.

The monitor output indicating the analysis-associated condition is produced by monitoring quantitative information, other than the detector output, that constitutes the chromatogram and that can change with time, and refers to the output that is concerned with the result of the chromatographic analysis. Typical examples of the monitor output indicating the analysis-associated condition include the output of an elution buffer conductivity monitor used in liquid chromatography to monitor the progression of gradient elusion. Other examples include a delivery pump pressure monitor output, a column oven temperature monitor output, a detector cell temperature monitor output, a temperature monitor output of a gradient monitoring electrical conductivity meter, a flow rate monitor output, and a monitor output that indicates the presence or absence of air bubbles in a flow passage.

When the chromatogram is displayed by superimposing these monitor outputs indicating the analysis-associated conditions over the detector output, abnormality that is difficult to discover by the detector output alone can be identified. For example, by checking pressure variations at the time of sample injection, it becomes possible to trace whether the sample injection has been done correctly. If the peak becomes small and the pressure at the time of sample injection becomes low, then it can be deduced that the amount of sample injection was insufficient. Further, when performing gradient extraction, by checking the conductivity at the time of sample injection it becomes possible to trace whether the column has been completely initialized or not. Accordingly, in the event of the occurrence of such phenomenon as the peak shape of the initial elution being bad or the reproducibility being poor, it can be easily determined whether gradient conditions are proper or not by checking the conductivity at the time of sample injection.

One feature of the present invention is that not only the monitor output indicating the analysis-associated condition but the detector output is also collected and recorded at every data sampling rate T2 over the period from the start to the end of the chromatographic analysis. That is, the detector output that should be analyzed in detail to obtain an analysis quantitative value is collected at every data sampling rate T1, while on the other hand, the analysis-associated condition is collected and recorded at every data sampling rate T2 to verify the validity of the data throughout the entire analysis process and, at the same time, the detector output is also collected and recorded, thus recording the time position relationship between the analysis-associated condition and the detector output while retaining the continuity of the chromatogram. In this way, with limited memory resources, not only can the chromatogram be analyzed in detail, but the continuity of the chromatogram can also be retained throughout the long analysis time, while recording the monitor output indicating the analysis-associated condition throughout the entire analysis process.

The data sampling rates T1 and T2 need only be set to satisfy the relation T1<T2, but otherwise can be set as desired according to the purpose of the analysis. In a series of measurements, the data sampling rate T1 may be varied for each sample injection in accordance with the amount of sample injection, etc. or may be fixed to a predetermined set value. The data sampling rate T2 is suitably set according to the kind of the analysis-associated condition. For example, the data sampling rate for monitoring the conductivity of the elution buffer may be set equal to the data sampling rate for sampling the detector monitor output over the entire analysis process. Further, the data sampling rate for monitoring the temperature, for example, may be set longer.

When setting T1 and T2 to respectively fixed values, T1 is set, for example, to about 100 ms, and T2 to about 500 ms. In the series of measurements from the start to the end of the chromatographic analysis, the data sampling rate T1 is set according to the continuously measured total analysis time, the sample volume injection, the number of samples, the memory capacity of the data collecting section, etc. The data sampling rate T2 is suitably set according to the kind of the analysis-associated condition and the total analysis time.

In a chromatographic analysis performed by continuously injecting samples, it is preferable to collect analysis history, such as control logs for sample injection and separation, an operation log recording any changes made to analysis conditions, and an error log, in addition to the quantitative information such as the detector output and the monitor output that can change with time. Displaying the continuously collected chromatogram and the analysis history on the same screen for monitoring is particularly advantageous for examining the analysis results. For example, by displaying the waveform 4 of the programmed gradient signal of FIG. 2(a) and the waveform 5 of the actual gradient monitor signal on the same screen, the actual gradient can be compared with the programmed gradient to determine whether the correct gradient has been accomplished or not.

In those days when chromatograms were recorded by connecting a pen recorder to a chromatography apparatus, it was often practiced to write comments directly on chart paper. In the present day also, there often arises a need to record a sudden event or idea along with the record of the measurement, though such a need is antithetical to the need for digital recording and digital signature. From the viewpoint of eliminating the possibility of data falsification, which is one of the problems that the present invention aims to solve, strict attention must be paid when recording optional comments. One feature of the present invention is the construction of a system that specifically permits the recording of optional comments which have the potential of threatening the objectivity of data. That is, the system enables optional comments to be entered using a mouse and a keyboard, for example, on the screen on which the detector output, the analysis-associated condition, etc. being collected continuously are displayed for monitoring. Such optional comments are recorded by being distinctly distinguished from other controlled operation logs, etc., and the time of writing and a sign indicating that it is non-rewritable are appended to the comments. Here, the comments may be allowed to be altered; in that case, the previous record is left as is and the time of alteration is appended.

Since the optional comments are written within the series of chromatograms being recorded from the start to the end of the chromatographic analysis, the contents of the comment and information indicating its position in the chromatogram to which the comments are written are collected as the optional comments by the second data collecting section. Examples of such optional comments to be collected include the operator's operations such as replenishment of the elution buffer, and opening/closing of the door of a column oven, or the like.

The data processor of the present invention manages the data by associating the data collected by the first data collecting section concerning the detector output for each sample injection with the data collected by the second data collecting section concerning the detector output and the monitor output, etc. indicating the analysis-associated condition over the entire series of analyses from the start to the end of the chromatographic analysis. Since the detector output for each sample injection and the monitor output, etc. indicating the analysis-associated condition are associated with each other as described, both data can be displayed on the same screen, and the detector output for each sample injection can be analyzed in detail by referring to the analysis-associated condition, etc. To associate the data collected by the first data collecting section concerning the detector output for each sample injection with the data collected by the second data collecting section concerning the detector output and the monitor output, etc. indicating the analysis-associated condition over the entire series of analyses from the start to the end of the chromatographic analysis, both data are managed, for example, within the same database.

The monitor output, etc. indicating the analysis-associated condition include, for example, the analysis history and the optional comments in addition to the monitor output indicating the analysis-associated condition.

The chromatography apparatus, which comprises the data processor of the present invention and the chromatogram display section which displays at least one output selected from the group consisting of the detector output that have been recorded by the data processor, the monitor output indicating the analysis-associated condition, the analysis history, and the optional comments, is not specifically limited in its configuration, the only requirement being that at least one of the outputs be displayed. For example, only the detector output collected and recorded by either one of the first and second data collecting sections may be displayed, or only the monitor output indicating the analysis-associated condition and collected by the second data collecting section may be displayed; alternatively, the various outputs may be displayed by switching from one to another. Further, by displaying arbitrarily selected two or more outputs with one superimposed on another along the same time axis, the chromatography apparatus that makes detailed analysis possible, as earlier described, can be achieved. In particular, displaying the chromatogram by superimposing the monitor output indicating the analysis-associated condition over the detector output collected and recorded by the second data collecting section is, as earlier described, effective in identifying abnormality that is difficult to discover by the detector output alone. When displaying two or more outputs by superimposing one over another as described above, combinations of arbitrarily selected outputs may be displayed by switching from one combination to another.

Thus, with limited memory resources, not only can the chromatogram be analyzed in detail, but the continuity of the chromatogram can also be retained throughout the long analysis time, while making it possible to monitor the analysis-associated condition throughout the entire analysis process. In particular, in the case of an analysis in which the detector and the pump require time to stabilize and thus the period for waiting the sample to be injected is long, a great deal of memory can be saved. Further, by collecting and recording the analysis history and/or the optional comments throughout the entire series of analyses from the start to the end of the chromatographic analysis, the data processor useful for eliminating the possibility of data falsification and verifying data validity can be provided.

For a further understanding of the present invention, an embodiment will be described with reference to the drawings.

EXAMPLE

FIG. 1 is a diagram illustrating the flow of information around the data collecting sections which constitute the characteristic data processor of the present invention. Here, the first data collecting section collects the detector output for each sampling injection at every data sampling rate T1. On the other hand, the second data collecting section collects and records the detector output throughout a series of analyses from the start to the end of the chromatographic analysis process, and collects and records at every data sampling rate T2 the output of a conductivity meter installed as a gradient monitor, the output of a temperature sensor installed near it, and the output of a pressure sensor installed in the flow passage near a delivery pump. The second data collecting section also collects and records optional comments and analysis history, such as control logs for sample injection and separation, an operation log recording any changes made to analysis conditions, and an error log, throughout the series of analyses from the start to the end of the chromatographic analysis process. In FIG. 1, the details of an A/D converter and an arithmetic processing unit, which are usually provided in the data processor, are omitted.

Figure 2:
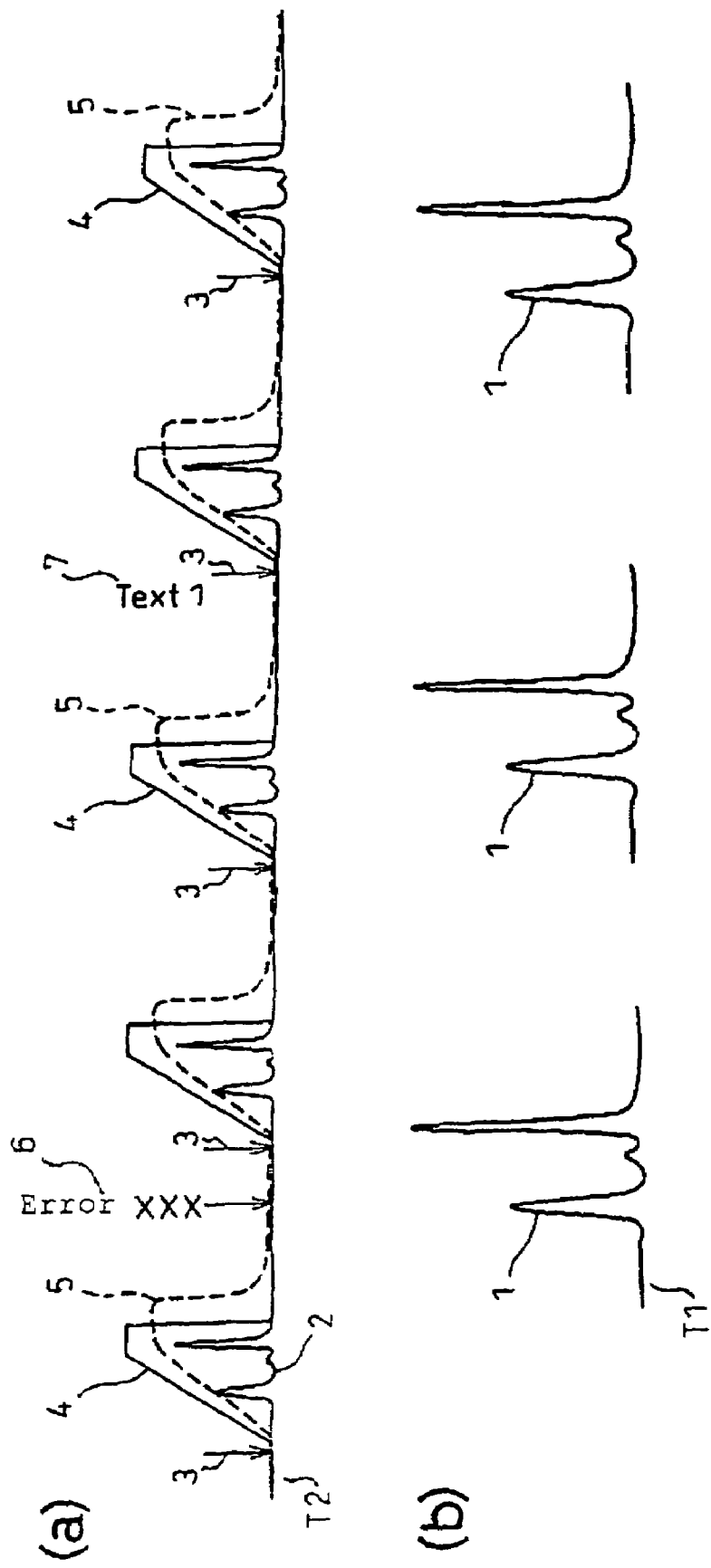
FIG. 2 is a diagram

FIG. 2 is a diagram showing the data processed by the data processor of the present invention and displayed on a chromatogram display. FIG. 2(a) shows a chromatogram produced by displaying the detector output 2, the analysis-associated condition (waveform 5 of actual gradient monitor signal), the analysis history (sample injection time 3, waveform 4 of programmed gradient signal, and error indication 6), and the optional comments 7 on the same screen along the same time axis throughout the entire series of analyses from the start to the end of the chromatographic analysis process. Here, the error indication 6 and the optional comments 7 each indicate one example of display (XXX indicates the type of error).

In FIG. 2(a), the signals are actually sampled at data sampling rates of about 0.5 second, but each signal appears as if it were a continuous quantity when displayed in a large time-scale chart. In the actual analysis using the data processor of the present invention, changes in the pressure monitor output and the temperature monitor output are also displayed.

FIG. 2(b) is a diagram schematically showing the detector output 1 recorded by the first data collecting section for each sample injection. FIG. 2(b) shows the detailed detector output for each sample injection, and each detector output is recorded independently of the others. The loss of continuity between the detector outputs is compensated for by the data of FIG. 2(a) FIG. 2(b) shows the detector outputs 1 for three samples, but it is also possible to display the detector output for one sample only; further, each detector output can be displayed simultaneously with the chromatogram shown in FIG. 2(a), for example, below the chromatogram.

It will be appreciated by those skilled in the art that while the invention has been described above in connection with particular embodiments and examples, the invention is not necessarily so limited and that numerous other embodiments, examples, uses, modifications and departures from the embodiments, examples and use may be made without departing from the inventive scope of this application.

The invention claimed is:

1. A data processor for use in chromatographic analysis in which a sample is injected into a separation column and is detected by a detector, comprising:

a first data collecting section which, for each sample injection, collects and records a detector output at every data sampling rate T1; and a second data collecting section which collects and records the detector output and a monitor output indicating an analysis-associated condition at every data sampling rate T2 over a period from the start to the end of the chromatographic analysis, wherein the data sampling rate T1 is shorter than the data sampling rate T2.

2. A data processor as claimed in claim 1, wherein the second data collecting section further collects and records analysis history.

3. A data processor as claimed in claim 1, wherein the second data collecting section further collects and records non-rewritable optional comments together with time of writing thereof.

4. A chromatography apparatus comprising:

a data processor as claimed in claim 1; and a chromatogram display section which displays at least one output selected from the group consisting of a detector output recorded by the data processor, a monitor output indicating an analysis-associated condition, analysis history, and optional comments.

* * * * *